United States Patent [19]

Zarowitz et al.

[11] Patent Number: 4,880,014

[45] Date of Patent: Nov. 14, 1989

[54] METHOD FOR DETERMINING THERAPEUTIC DRUG DOSAGE USING BIOELECTRICAL RESISTANCE AND REACTANCE MEASUREMENTS

[76] Inventors: Barbara J. Zarowitz, 6045 Shillingham Dr., West Bloomfield, Mich. 48033; Diana L. Twyman, 1978 Villa, Birmingham, Mich. 48008

[21] Appl. No.: 160,589

[22] Filed: Feb. 26, 1988

Related U.S. Application Data

[63] Continuation-in-part of Ser. No. 85,850, Aug. 14, 1987, abandoned.

[51] Int. Cl.$^4$ .................................................. A61B 5/05
[52] U.S. Cl. .................................. 128/734; 364/413.1; 604/50
[58] Field of Search ................... 128/693; 604/734, 50; 364/413.07, 413.11, 413.1

[56] References Cited

U.S. PATENT DOCUMENTS

| | | | |
|---|---|---|---|
| 4,109,645 | 8/1978 | Bacchelli | 128/734 |
| 4,557,271 | 12/1985 | Stoller et al. | 128/734 |
| 4,562,843 | 1/1986 | Djordjevich | 128/672 |
| 4,793,362 | 12/1988 | Tedner | 128/734 |
| 4,794,934 | 1/1989 | Motoyama et al. | 128/734 |

OTHER PUBLICATIONS

Shizgal et al., "Total Body Potassium in Surgical Patients" Surgery, Jun. 1974.
Dahlgren et al., "Gentamicin Blood Levels etc.", AAC, Jul. 1975.
Sawchuk, "Pharmacokinetics of Dosing Regimens etc." JPB 1976, vol. 4 No. 2.
Schentag et al., "Comparative Tissue Accumulation etc." JAC, 1978, vol. 4, supp. A.
Lesar et al., "Gentamicin Dosing Errors etc.", JAMA, Sep. 10, 1982.
Kohlhepp et al., "Nephrotoxicity etc.", JID, Apr. 1984.
Matzke et al., "Gentamicin and Tobraycin etc.", DICP, Jun. 1983, vol. 17.
Lusaki et al., "Validation of tetrapolar etc.", JAP 1986, 60(4):1327-32.
Shizgal, "Body composition of patients etc." Cancer, 1985 Supp., vol. 55.
Lukaski et al., "Assessment of Fat-Free Mass etc." AJCN, Apr. 1985, vol. 41, pp. 810-817.
Freioman et al., "Rational Therapeutic Drug Monitoring," JAMA, Oct. 1986, vol. 255, No. 16.
McDougall et al., "Body Composition Measurements etc.," Surgical Forum, 1986, vol. 32.
Lukaski et al., "Theory and validation etc.," INTL Symposium, 1986, Broohven lab.
Kushner et al., "Estimation of total body water etc.," JCN, Sep. 1986.
Nyboer et al., "Nontraumatic Electrical Detection etc.", Proceedings of the VI ICEBI, pp. 381-384, 1983.
Medical & Biological Engineering & Computing; "Quantitative Interpretation of Arterial Impedance Plethysmorgraphic Signals"; M. Y. Jaffrin and C. Vanhoutte; Jan., 1979; pp. 2-10.
"Quantitative Parameters of Body Composition and Theophylline Deposition", Annals of Allergy, 1988.
"Bioelectrical Impedance (BI)-Predicted Drug Doses", B. J. Zarowitz, D. Twyman, Clinical Pharmacology and Therapeutics 1988;43:189.

Primary Examiner—Francis Jaworski
Assistant Examiner—George Manuel
Attorney, Agent, or Firm—Dykema Gossett

[57] ABSTRACT

A method for determining a dosage regimen for a drug. Resistance (R) and reactance (Xc) are measured by bioelectrical impedance analysis with an impedance plethysmograph. Personal characteristics of a subject are ascertained and recorded along with the measured values of R and Xc. A technique for generating equations which relate the measured values of R and Xc and selected personal characteristics to pharmacokinetic parameters such as volume of distribution (V), elimination rate constant (K), and clearance (CL) for a particular drug are provided. These equations are used with the measured values of R and Xc and certain personal characteristics to determine predictive values for the desired pharmacokinetic parameters. These predictive values are then used to determine an appropriate drug dosage regimen for the patient.

11 Claims, 1 Drawing Sheet

METHOD FOR DETERMINING THERAPEUTIC DRUG DOSAGE USING BIOELECTRICAL RESISTANCE AND REACTANCE MEASUREMENTS

This application is a continuation in part of U.S. patent application Ser. No. 085,850 filed on Aug. 14, 1987, now abandoned.

FIELD OF THE INVENTION

The present invention relates generally to methods for determining drug dosage requirements in biological subjects and, more specifically, to methods for determining therapeutic dose and dosing interval for individualized dosage regimens.

BACKGROUND OF THE INVENTION

The prompt and accurate initiation of drug therapy to a patient is essential in the treatment of many medical conditions. An inappropriate dosage regimen may produce therapeutic failure as the result of subtherapeutic drug levels or, alternatively, due to toxic drug levels (overdose). Determining therapeutic dosage is often complicated by the therapeutic index of a drug. In clinical medicine, the therapeutic index of a drug is the ratio of the highest potentially therapeutic concentration to the lowest potentially therapeutic concentration. Thus, therapeutic index defines the acceptable range of blood serum concentration for an individual drug. As used herein, the term "therapeutic" when used in connection with "drug dosage," "drug dosage regimen" and "concentration," etc. shall be defined, without limiting its customary meaning, as the appropriate drug dosage necessary to provide a desired effect without producing concomitant adverse affects.

Many drugs, such as aminoglycosides, theophylline, gentamicin, and lithium, have narrow therapeutic ranges. The proper administration of these drugs requires an accurate prediction of the relationship between dose, dosing interval and the resulting blood concentration of the drug in the patient. "Recommended dosage" information is often provided by a drug manufacturer or is available from a drug compendium or the like. for some drugs, this information is sufficient such that no further predictive determination is necessary. In these instances, the recommended dosage is simply administered without further consideration of serum concentrations. However, when it is necessary to initiate drug therapy using one or more drugs having narrow therapeutic ranges, such as aminoglycosides, establishing a therapeutic dosage regimen is quite complex.

To assist the medical team in making this determination, various predictive methods have been developed by others in the past for calculating an appropriate dose and dose interval for drug administration. Due to inherent inaccuracies of prior art methods, it has been held that an appropriate dosage regimen should be derived cautiously where possible by administering a loading dose and then developing a dosage regimen slowly by raising serum concentrations until satisfactory results are obtained. As those skilled in the art will appreciate, however, a conservative exploration of therapeutic drug levels is not always possible and aggressive drug therapy is often necessary. This is particularly true for gram negative infections where the first 24 hours of treatment may be critical.

It will be understood by those skilled in the art that the dosage regimen includes the quantity of drug administered (dose) and the frequency of administration (dosing interval). It will also be appreciated that various methods of drug delivery are available such as intravenous or intraperitoneal injection or the like and that often drugs will be introduced by infusion. The dosing profile of a drug is determined by its pharmacokinetic characteristics.

The initiation of drug therapy includes the administration of an initial loading dose and subsequent interim maintenance doses at periodic intervals to achieve therapeutic "peak" and "trough" blood concentrations. In conventional methods, a determination of the dosage regimen typically involves the use of nomograms and dosing guidelines derived from population averages. Typically, measured serum drug concentrations will not be available before a maintenance dose is required.

Prior art predictive dosing methods for aminoglycoside antibiotics include the dosing chart of Sarubbi-Hull, the dosing technique of Dettli, the dosing nomogram of Chan and the Rule of Eights. In general, these methods utilize the patient's weight to estimate volume of distribution (V). Creatinine clearance is calculated from the patient's serum creatinine level to estimate an elimination rate constant (K). The use of K and V in drug dosage determination will be well-known to those of average skill in the art. Some methodologies employ ideal body weight while others utilize actual body weight. It will be understood by those in the art, that in reality each patient exhibits a singular ability to eliminate a drug (K) and a characteristic drug volume of distribution (V) for a particular drug. Hence the values of both K and V for a patient may deviate significantly from population-based averages. It has been shown by others that these conventional methods result in subtherapeutic and potentially toxic blood concentrations in many patients when used for the administration of certain drugs. In particular, it is known that nomograms and dosing guidelines are poor predictors of the elimination rate constant (K). Hence, there is a need for a more accurate method for predicting drug serum concentration such that therapeutic dosing can be achieved during initial drug therapy.

Following the initiation of drug therapy, blood assays are typically performed to determine analytically the serum concentration of the therapeutic agent. New values for K and V are then derived using the serum drug concentration data. Dosage adjustment is then effected as needed, based on the new values of K and V. Although this method of drug dosage adjustment is preferable over continued use of unindividualized predictive dosing determinations, blood analysis suffers from several drawbacks. Repeated venupuncture, which is generally used to obtain a blood sample, may cause patient discomfort with an associated risk of nosocomial infection. Also, the frequency of blood sampling may require periodic transfusions to prevent anemia.

An additional factor which militates against the use of blood assays to determine dosage regimen is the cost associated with blood analysis. In order to obtain blood data, a physicians order must be prepared pursuant to which a trained phlebotomist must draw the blood sample. The sample is then carefully labeled with identifying information and sent to a laboratory for testing. Laboratory technicians must then separate and isolate the blood serum through centrifugation or the like. Utilizing a variety of analytical methods, the serum concentration of the drug is then determined usually in duplicate to enhance the accuracy of the testing procedure. This information must then be conveyed to the medical team so that it can be used to evaluate and adjust the dosing regimen. It has been estimated that the cost of analyzing a single blood specimen in a hospital may exceed one hundred dollars.

Moreover, and serving to further impede dosage determination, the data obtained from the blood assay may be meaningless for a number of reasons. It will be appreciated by those skilled in the art that blood assaying is a complex and laborious task. It has been estimated that up to 40% of all blood samples analyzed for serum drug concentration yield data which cannot be used to determine an appropriate dosage regimen. Therefore, it would be desirable to provide an inexpensive method for determining a dosage regimen which can be performed without complicated assays or highly skilled technicians. To that end, we have discovered an inexpensive method of determining dosage requirements which provides accurate, individualized dosing data by noninvasive means.

SUMMARY OF THE INVENTION

In accordance with the present invention there is provided a novel method of drug dose determination by which individualized K and V values are determined using bioelectrical impedance analysis. In substance, a human subject is connected to a bioelectrical impedance analyzer which is activated to generate an excitation current having a preselected amperage and frequency. As the excitation current flows from the current electrodes through the patient's body to the detector electrodes, the drop in voltage is detected by the detector electrodes and this voltage drop is measured by the impedance analyzer. The resistance (R) and reactance (Xc) components of the patient's bioelectrical impedance (Z) are then determined and displayed by the analyzer. Either before or after the bioelectrical impedance analysis is conducted, the patient's personal characteristics including the patient's age, sex, weight and height are ascertained and recorded. In the broadest aspect of the invention, the values obtained for the patients R and Xc are then used in association with the patient's personal characteristics and the pharmacokinetic properties of the drug to be administered to calculate the patient's elimination rate constant (K) and the patient's volume of distribution (V) for the preselected drug to be administered. The individualized values of K and V are then used to determine dose and dosing interval to achieve a therapeutic drug dosage regimen for the patient. Thus, the present invention provides a noninvasive method by which a therapeutic dosage regimen can be determined which is individualized to the patient. By allowing a target serum drug concentration to be attained non-invasively, the present invention presents numerous advantages over prior art drug dosing techniques.

It is a significant advantage of the present invention to permit V to be calculated for use in determining an appropriate loading dose. An appropriate dose can be selected initially by determining K and V, individualized for each patient before therapy is initiated. A further advantage of the invention is that it permits K and V to be determined repeatedly without patient discomfort and without encoutering the risks inherent in blood sampling, since direct chemical assay of serum levels is not required. An additional advantage of the present invention is a significant reduction of medical costs by eliminating the need for numerous blood assays to be performed. In addition, the accuracy of the present invention effectively conserves drug resources and may reduce morbidity and mortality which may be caused by inaccurate dosing determinations. Furthermore, by providing an accurate method for determining a therapeutic drug dosage regimen, the present invention can eliminate prolonged hospitalization occasioned by subtherapeutic or toxic drug dosage.

Thus, the present invention provides a method for determining a therapeutic dosage regimen which provides optimum accuracy and which reduces the occurrence of subtherapeutic or toxic drug doses which otherwise may occur due to an erroneous prediction of loading dose or inaccurate blood assay information. These and other meritorious features of the present invention will become apparent from the following detailed description of the preferred embodiment, the appended claims and the accompanying drawings.

DETAILED DESCRIPTION OF THE PREFERRED EMBODIMENT

As used herein, the foregoing definition of "therapeutic" shall be used, but is to be understood that drug therapy in a given case may have a number of objectives including the healing or curing of a disease or illness. Thus, it is to be understood that the present invention is useful in the administration of a drug to an individual, irrespective of the goal of drug treatment. This may include the administration of prophylactic agents, anesthetics, or the like. Hence, the terms "drug" and "therapeutic" are to be broadly construed.

Figure 1:
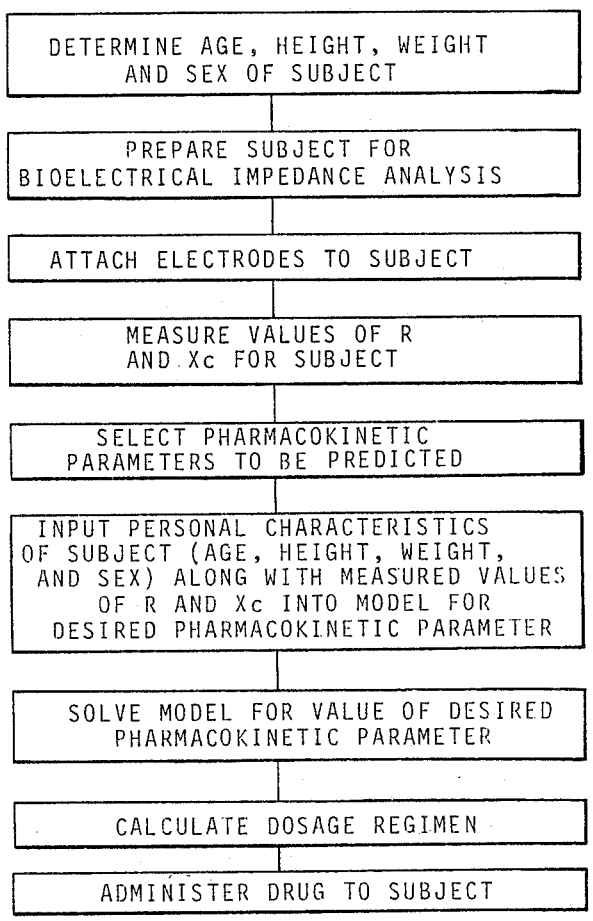
FIG. 1 is a flow chart illustrating the preferred steps of the present invention in one embodiment.
Figure 2:
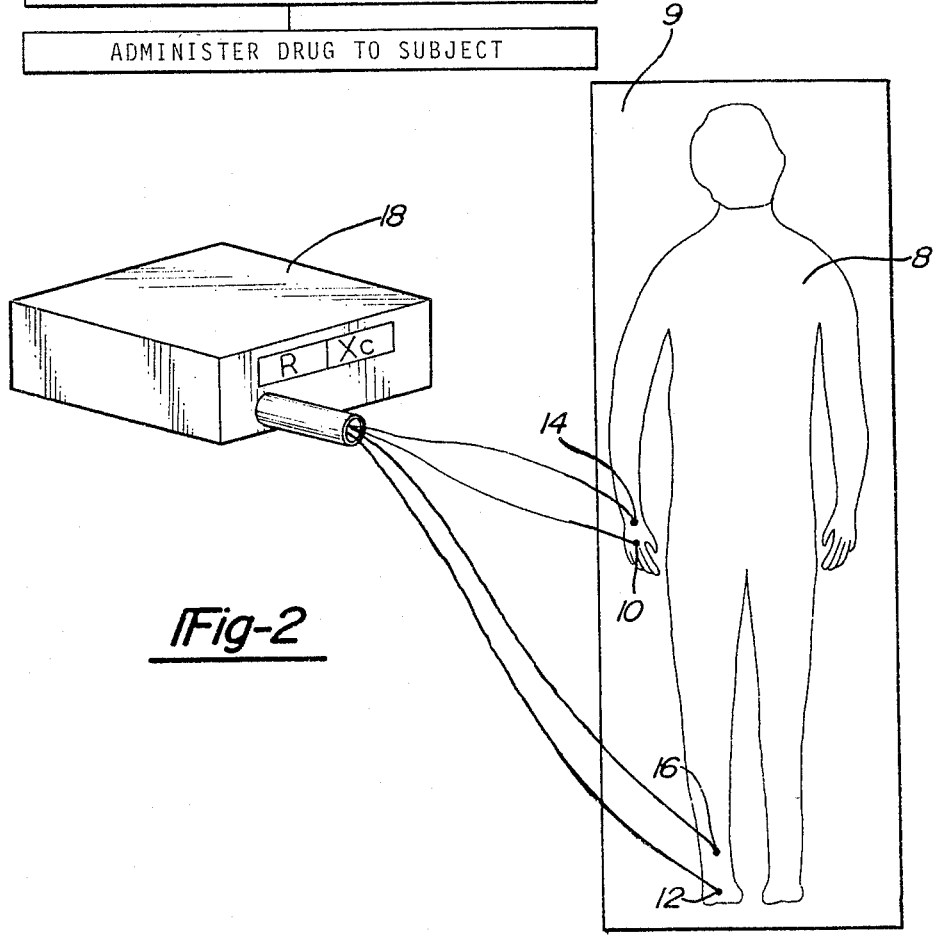
FIG. 2 is a diagrammatic illustration of a patient having current electrodes and detector electrodes of a four electrode bioelectrical impedance plethysmograph attached ipsilaterally in accordance with the present invention.

Referring now to FIGS. 1 and 2 of the drawings, in the first step of the present invention, personal characteristics including the age, height, weight and sex are determined for patient 8 using conventional techniques. Patient 8 is preferably a human subject, although the present invention may be useful on animal subjects. Patient 8 is then prepared for bioelectrical impedance analysis. This includes placing patient 8 in the supine position on a substantially electrically insulative surface, for example, canvas or cloth cot 9. For the preferred electrode arrangement, at least one of the patient's feet is exposed for electrode attachment. The patient's arms are positioned such that they are spaced at least slightly from the torso. Similarly, the patient's legs are spaced slightly apart. In the preferred electrode arrangement, current electrodes 10 and 12 and detector electrodes 14 and 16 are positioned ipsilaterally on patient 8 as shown in FIG. 2. A suitable 4-terminal impedance plethysmograph 18 for use in the present invention may be obtained from RJL Systems, Detroit, Mich. Other impedance plethysmographs are suitable for use herein, provided the principles of the present invention are faithfully observed. Also, alternative electrode arrangements may be used.

Once patient 8 is properly positioned on insulative surface 9, those areas of the patient's skin where the electrodes are to be connected are cleaned thoroughly with alcohol to provide good electrical contact. To this end, a coating of electrolyte gel is applied to each electrode surface or pre-gelled electrodes are utilized. Other types of electrodes or electrode tape may be suitable. The four electrodes are then attached to the patient in the following manner. Current electrode 10 is attached to the dorsal surface of the patient's right hand at the distal metacarpals. Current electrode 12 is attached to the patient's right foot at the location of the distal metatarsals. Detector electrode 14 is connected to the patient's right wrist at the right pisiform prominence. Detector electrode 16 is connected to the patient's right ankle between the medial and lateral malleoli. The relative positions of current electrodes 10, 12 and detector electrodes 14, 16, as shown in FIG. 2 of the drawings, create an electrical pathway between the patient's right arm and the patient's right foot through which current will flow.

It will be understood that the human body is an electrical conductor through which an applied electrical current will flow. The opposition offered by the body to the flow of alternating current of a given frequency is the electrical impedance of the body or the bioelectrical impedance. Bioelectrical impedance is a combination of resistance and reactance components and is measured in ohms. For the purposes of bioelectrical impedance, the resistance of lean tissues having a high water content is low. Dry electrically insulating tissues such as adipose tissue and bone are highly resistive. Body water contains a large number of electrolytes and is thus quite conductive. Also, while the intracellular and extracellular body fluids conduct an electrical current quite readily, cell membranes which comprise a layer of nonconductive lipids interposed between two layers of electrically conductive polar molecules act as capacitors providing capacitive resistance. The reactance component or vector of bioelectrical impedance reflects the resistance to electrical flow caused by this capacitance. Thus, an electrical circuit is created in which the subject's body is a series of circuit elements having a resistance (R) and a reactance (Xc) which can be measured. It will be understood by those skilled in the art that electrical impedance (Z) is equal to the voltage (E) divided by the current (I). It will also be understood that resistance (R) is the sum of the in-phase vectors and that reactance (Xc) is the sum of the out-of-phase vectors. The determination of the R and Xc components of Z are preferably determined by impedance plethysmograph 18 in the conventional manner.

After patient 8 and electrodes 10, 12, 14, 16 are in position, an alternating excitation current is introduced or flowed through patient 8 by energizing current electrodes 10 and 12. While the strength of the current and frequency may vary, we prefer to use a radio frequency excitation current of about 800 microamps and a frequency of from about 100 Hz to 1 MHz and most preferably about 50 kHz, although other amperages and frequencies may be suitable or even desirable in some applications. In other words, another arrangement of frequency and current and electrode arrangement may be used so long as it is substantially painless and similarly avoids any unwanted physiological effects or undesirable "skin" effects. As the electrical current flows from current electrodes 10 and 12 to detector electrodes 14 and 16, detector electrodes 14 and 16 detect the drop in voltage. Impedance plethysmograph 18, which includes phase-sensitive electronics, determines the values of the R and Xc components of the patient's measured impedance (Z). The values for R and Xc are preferably displayed directly by the impedance plethysmograph 18. While the arrangement of electrodes depicted in FIG. 2 is ipsilateral, contralateral or other arrangements may be used provided the excitation current flows through a substantial portion of the subject's body such that accurate values for R and Xc are obtained. The determination of R and Xc for a patient by impedance analysis and methods and apparatus by which this determination is made will be well known and understood by those skilled in the art. Thus, with reference to FIG. 1 of the drawings, the first step in the present invention is the determination of the personal characteristics of patient 8; the second step is the preparation of patient 8 for bioelectrical impedance analysis; the third step includes the appropriate attachment of electrodes to patient 8, and the fourth step comprises determining the values for R and Xc for patient 8 by bioelectrical impedance analysis.

It has been shown by others that the values of R and Xc obtained in the manner described are a function of the body volume make-up of patient 8. That is, the proportionate volumes of a subject's lean body tissue mass (fat free mass), total body water, body fat, intracellular mass and extracellular mass determine the patient's impedance (Z) and thus the values of R and Xc. In Table I which follows, standard equations are set forth which relate R and Xc in association with personal characteristics for these various body volumes.

TABLE I

RELATIONSHIP OF BODY RESISTANCE (R) AND REACTANCE (Xc) TO BODY VOLUMES

| | Source |
|---|---|
| Males: | |
| Total Body Water = TBW = $0.396 \left( \frac{H^2}{R} \right) + 0.143 \, (WT) + 8.399$ | Kushner, et al. AJCN 1986: 44, 417–424 |
| Females | |
| Total Body Water = TBW = $0.382 \left( \frac{H^2}{R} \right) + 0.105 \, (WT) + 8.315$ | |
| Fat Free Mass = | |
| FFM = $4.033 + 0.734 \left( \frac{H^2}{R} \right) + .096 \, (Xc) + 0.116 \, (WT) + 0.878 \, (Gender)$ | |

TABLE I-continued
RELATIONSHIP OF BODY RESISTANCE (R) AND REACTANCE (Xc) TO BODY VOLUMES

| | Source |
|---|---|
| where Gender is 1.0 where the subject is male<br>where Gender is 0.0 where the subject is female | Lukaski, et al.,<br>FASE B |
| Body Cell Mass = BCM = $FFM/(1.69 + 1.4)\frac{H^2}{WT/Xc}$ | McDougall and Shizgal, Surg. Forum, Vol. XXXVI p. 42–44, 1986. |
| $\frac{ECM}{BCM} = 2.4 + \frac{34.8}{XC} - 5.97 \times 10^{-5} (H^2)$ | |
| $\frac{Nac}{Ke} = 1.87 + \frac{34.1}{Xc} - 4.66 \times 10^{-5} (H^2)$ | |
| Fat Free Mass (FFM) = Lean Body Mass (LBM)<br>Fat Free Mass (FFM) = Total Body Weight (WT) − Body Fat<br>Body Fat (fat mass) = Total body Weight (WT) − FFM<br>Extracellular Mass (ECM) = LBM − Body Cell Mass (BCM)<br>Body Cell Mass (BCM) = Intracellular Mass (ICM) | |

| | |
|---|---|
| H = Height of Subject (cm) | Nae = Exchangeable Sodium (mEq) |
| R = Resistance (ohms) | Ke = Exchangeable Potassium (mEq) |
| WT = Weight of Subject (kg) | ECM = Extracellular Mass (kg) |
| Xc = Reactance (ohms) | TBW = Total Body Water (kg) |
| FFM = Fat Free Mass (kg) | LBM = Lean Body Mass (kg) |
| BCM = Body Cell Mass (kg) | BF = Body Fat (kg) |
| | ICM = Intracellular Mass (kg) |

The derivation of these equations as well as their corroboration can be found in articles authored by the respective researchers and others. In the most preferred embodiment of the present invention, relationships have been identified which are used to determine volume of distribution (V) and elimination rate constant (K) for patient 8 for a preselected drug using the measured values of R and Xc, the patient's personal characteristics, and distribution and drug elimination characteristics of the preselected drug to be administered. In the preferred embodiment of the present invention, equations for predicting volume of distribution (V) and elimination rate constant (K) for a preselected drug are generated using stepwise multiple linear regression techniques. Each quantity, V and K, are considered separately as a single dependent variable. A set of 14 independent variables are then preferably evaluated for inclusion into a linear model for predicting V and K. The preferred independent variables are:

TABLE II

| | |
|---|---|
| sex | |
| age | height$^2$/(weight × resistance) |
| height | 1/weight |
| weight | reactance/weight |
| lean body weight | height/weight |
| reactance | reactance/resistance |
| resistance | (reactance/resistance)$^3$ |
| phase angle | |

With respect to the sex of patient 8, this variable is assigned a value of 1.0 where patient 8 is male and 0.0 where patient 8 is female. Age is measured in years, reactance is measured in ohms, phase angle=arc tan multiplied by reactance over resistance in degrees, weight is measured in kilograms, height is measured in centimeters and resistance is measured in ohms. Hence, the appropriate measurements and calculations are made to determine the values of these preferred variables. It is to be understood that other independent variables may be appropriate for consideration including those variables set forth in connection with the discussion of body volumes. The generation of the model for determining V and K follows a prespecified algorithm. A number of stepwise linear regression routines are currently available, for example "SAS" (SAS User Guide: Statistics, Version 5 edition) which may be obtained from SAS Institute, Inc., "BMPD" (Biomedical Data Processing) and "SPSS" (Statistical Programming for the Social Sciences). These programs utilize what is known as the backwards stepping mode which initially starts with all variables in the model and then deletes variables one at a time as will be more fully explained. This method identifies sets of variables which considered jointly are statistically significant but which when considered separately may be not statistically significant. It will be understood that some of the aforementioned variables are non-linear functions of the other variables.

The backward stepping algorithm initially fits a linear least-squares regression model to the entire set of 14 independent variables. At step 1, the variable with the smallest contribution to the model (lowest partial correlation) is considered. If it is statistically significant with a p-value less than 0.05 it is retained in the model and the process stops. If it is not significant (p is greater than 0.05) it is dropped from the model and the algorithm proceeds to the next step. The remaining variables are then considered and again the variable with the smallest contribution is identified. If it is statistically insignificant. it is dropped and the process continues. If it is statistically significant, it is retained and the process stops. The end result of the algorithm is a regression model where each independent variable included on the model is statistically significant. This process is used for the determination of each dependent variable, V and K. Thus, actual values of V and K for the preselected drug for a test population are used in this manner to calculate equations for predicting V and K using the aforementioned personal characteristics of patient 8, preferably using the independent variables of Table II. The same process may be used to determine a model for predicting clearance (CL).

Actual values of V and K for a test or sampling population are calculated in the customary manner for a preselected drug. Volume of distribution may be calculated by the Sawchuk-Zaske method which is described in "Pharmacokinetics of Dosing Regimens Which Utilize Multiple Intravenous Infusion: Gentamicin in Burn Patients", J Pharmacokin Biopharm 1976; 4:183–95 or by application of non-linear regression programs such as "Micrononlin." The actual value of elimination rate constant (K) and the value of (V) are, however, preferably determined by non-linear regression analysis of serum concentration data for each patient of the sampling population using software marketed under the trademark "Micrononlin" which may be obtained from Elite Software, Pittsburgh, Pa. Other non-linear regression programs such as "Nonlin" which is a computer program for parameter estimation in non-linear situations developed by the Upjohn Company, "STRIP" which may be obtained from Micromath, Inc. or "CSTRIP" as described in "CSTRIP," a Fortran IV Computer Program for Obtaining Initial Polyexponential Parameter Estimates", J Phar Sci 65: 1006–10 1976, are suitable. Model independent programs such as "Lagran" as described in "Lagran Program for Area and Moments in Pharmacokinetic Analysis", Comput Programs Biomed 1983; 16: 203–16, can also be used to estimate pharmacokinetic parameters from serum concentration data. Other equivalent programs will be known by those skilled in the art. Therefore, in one embodiment, the present invention includes subjecting this actual data for a preselected drug to linear regression analysis to obtain standard values for V and K. These values are then used preferably with the aforementioned independent variables in Table II to obtain a model using stepwise multiple linear regression techniques for volume of distribution (V) for the preselected drug and a model for elimination rate constant (K) for the preselected drug. This has been carried out for 2 drugs of particular interest, gentamicin and theophylline. In addition, drug clearance (CL) may be measured for a preselected drug and a predictive model generated in the aforementioned manner using the preferred independent variables described above. Such a model for clearance (CL) was generated for theophylline. While in the most preferred embodiment the aforementioned preferred independent variables are used in the present invention to generate predictive models, it is to be understood that the standard variables and others set forth in Table II herein could be utilized in the present invention to generate similar predictive models for substantially any drug.

The preferred equation for determining volume of distribution (V) for gentamicin derived in accordance with the present invention is as follows:

Equation 1
$$V = 0.197 + 0.004(\text{age}) - 0.044(\text{reactance}) - 9.935(\text{phase angle}) + 1.315(\text{height/weight}) - 1.678(\text{height}^2/(\text{weight} \times R)) - 121.730(1/\text{weight}) + 587.580(\text{reactance}/R)$$

The equation generated for determining elimination rate constant (K) for gentamicin is as follows:

Equation 2
$$K = 0.802 - 0.208(\text{sex}) - 0.007(\text{age}) + 0.039(\text{reactance}) + 7.285(\text{phase angle}) + 1.925(\text{height}^2/(\text{weight} \times R)) + 205.613 (1/\text{weight}) - 1.858 (\text{height/weight}) - 434.405 (\text{reactance}/R)$$

The equation generated for volume of distribution (V) for theophylline is as follows:

Equation 3
$$V = -65.64 - 1.03(\text{age}) - 1.05(\text{height}) + 2.54(\text{lean body weight}) - 5530(1/\text{weight}) + 129(\text{reactance/weight}) + 1863(\text{reactance/resistance}) - 54300(\text{reactance/resistance})^3$$

The equation for elimination rate constant K for theophylline is as follows:

$$K = 0.03 - 9.78(1/\text{weight}) \qquad \text{Equation 4}$$

The equation generated for clearance (CL) for theophylline is as follows:

Equation 5
$$CL = -65.17 + 0.98(\text{height}) - 1.95(\text{lean body weight}) + 3.15(\text{reactance}) - 0.38(\text{resistance}) + 1.08(\text{weight}) + 8280(1/\text{weight}) - 95(\text{reactance/weight}) - 754(\text{reactance/resistance}) - 6200(\text{reactance/resistance})^3$$

It will be understood by those skilled in the art, that the present invention is useful for substantially any drug and that for many drugs, population-based values of V and K are available which can be used in connection with the present invention to generate models for predictive determination of V and K. It may also be possible to use less than all of the aforementioned independent variables in the present invention. Hence, the next step of the present invention includes the use of models derived in accordance with the present invention to determine predictive values of K and V for a preselected drug for patient 8. Typically, the derivation of these equations for a particular drug will occur long before treatment of patient 8 with the preselected drug occurs. It will be recognized, that once derived for a particular drug, these models can be used for that particular drug with virtually any patient. For example, once the predictive values of K and V for gentamicin for patient 8 have been determined using the models derived in accordance with the present invention, these values of K and V which have been determined non-invasively are used to calculate a therapeutic drug concentration, preferably based on trough and peak serum concentrations. Dosing interval may be calculated in the following manner:

$$(\text{Dosing interval} = -1/K \ln (\text{predose/postdose}) + t') \qquad \text{Equation A}$$

where K is the elimination rate constant found using the model of the present invention, predose is the desired trough serum concentration in micrograms/milliliters, postdose is the desired peak serum concentration in micrograms/milliliter and t' is the infusion time during which the drug is infused to the patient. Other calculations using the V and K values of the present invention may be suitable. Dose may be then determined using the following formula:

$$(\text{Dose} = KV(\text{postdose conc.}) \frac{1 - e^{-Kt}}{1 - e^{-Kt'}} \quad \text{Equation B}$$

where K is the elimination rate constant found using the model of the present invention, T is the dosing interval derived in the foregoing dose interval equation and t' is the infusion time.

It is to be understood that in the broadest sense the present invention provides a method for determining a dosage regimen by measuring a patient's bioelectrical impedance, and using this information to determine a dose and dosing interval which will provide a therapeutically desirable drug serum profile. Not only are there several ways in which the individualized values of K and V can be used to determine dose and dosing interval, the derivation of K and V based on measured values of R and Xc may also be obtained through various calculations.

Therefore, a method for determining the dose and dosing interval for a drug to produce a preselected serum concentration profile of the drug in a patient is provided by the present invention which in one embodiment includes the steps of developing equations to predict V, K and preferably CL, which include at least one of the independent variables of Table II; determining the age, sex, weight, and height of the subject; measuring the bioelectrical impedance of the patient using a bioelectrical impedance plethysmograph; determining the resistance and reactance components of the measured bioelectrical impedance; calculating the values of volume of distribution (V) and elimination rate constant (K) and preferably clearance (CL) using the aforementioned equations and the personal characteristics of the subject; selecting a therapeutic serum concentration profile for the patient; calculating the dose and dosing interval for the preselected drug to produce the desired serum drug concentration profile in the patient using the calculated values of V, K and preferably CL; and administering the preselected drug in accordance with calculated dose and dosing interval.

In more detail, in one embodiment of the present invention, actual values for V, K and preferably CL for a preselected drug are compiled for a test population and the data is subjected to linear regression analysis. Using the preferred independent variables of Table II, the values of R, Xc and personal characteristics of the patient population from which actual values for K, V, and CL have been obtained, a predictive model for determining K, Xc and CL for the preselected drug is generated using the aforementioned statistical techniques. A patient or subject having unknown values of K, V and CL who is to be treated with the preselected drug is then evaluated to obtain the patient's height, weight, age and sex. The patient is placed on a flat, electrically insulative surface and electrodes are attached to the patient's skin. The electrode cables are then attached to an impedance plethysmograph. An excitation current is introduced through the patient's body and resistance and reactance components of the patient's bioelectrical impedance are displayed by the plethysmograph and recorded. Using the measured values of resistance and reactance along with relationships of the personal characteristics of the patient, i.e., height, weight, age and sex, values for V, K, and CL are calculated with the equations for the preselected drug which were previously generated. Any other desired pharmacokinetic properties are also determined at this time. A desired concentration of the preselected drug is chosen based on literature and experience regarding the concentration necessary to obtain a therapeutic response. Using the impedance predicted values of K, V, CL and any other desired pharmacokinetic parameters, standard pharmacokinetic equations are used to formulate a correct dosage regimen necessary to obtain the desired concentration. The calculated dosage regimen is then administered to the patient upon physician's orders.

As will be understood by those skilled in the art, other pharmacokinetic properties of the preselected drug in addition to volume of distribution V, elimination rate constant K and clearance CL may be appropriate for determining an appropriate dosage regimen for patient 8 in a particular case. The utilization of this additional pharmacokinetic information is contemplated as falling within the scope of the present invention.

Thus, it is apparent that there has been provided in accordance with this invention, a method for determining therapeutic drug dosage requirements by using bioelectrical impedance measurements which fully satisfies the objects, aims, and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations. The present invention is further illustrated through the following examples which are no way intended to limit or restrict the scope of the invention.

EXAMPLE I

The following examples demonstrate, comparatively, pharmacokinetic parameters and calculated dosage regimens for prior art dosing methods against the bioelectrical impedance determined dosage regimens of the present invention. Twelve human subjects participated in the following study. The resistance (R) and the reactance (Xc) of each patient was measured using a four-terminal impedance plethysmograph. During the measurement, the subjects were placed in the supine position on an insulative surface. The electrodes were attached in the following manner. Those areas of the patient's skin where the electrodes were to be connected were cleaned thoroughly with alcohol. The four pre-gelled electrodes were then attached to the patient such that one current electrode was attached to the dorsal surface of the patient's right hand at the distal metacarpals, one current electrode was attached to the patient's right foot at the location of the distal metatarsals, one detector electrode was connected to the patients right wrist at the right pisiform prominence, and one detector electrode was connected to the patient's right ankle between the medial and lateral malleoli. An excitation current of 800 microamps and frequency of 50 kHz was then applied and R and Xc values obtained. Serial blood samples were obtained, for all twelve patients from an intravenous catheter placed in their arm. Samples were drawn immediately before the third regularly scheduled dose of gentamicin. The dose of gentamicin was infused over 30 minutes and followed by blood samples drawn at 0.5, 1, 3, 5, 7, and 12 hours after the end of the infusion. The blood was centrifuged and the serum separated and frozen at −20 degrees C. until the time of assay.

Serum samples were assayed in duplicate by enzyme mediated immunoassay technique (EMIT) with interday and intraday coefficients of variation of less than 5% at concentrations within the usual range (i.e., 2-10 mcg/ml). Serum concentrations for all twelve patients fell within this range.

The elimination rate constant was determined by nonlinear regression analysis of the serum concentration data for each patient using Micrononlin (Micrononlin, Elite Software, box 11223. Pittsburgh. PA 15238).

Volume of distribution was calculated by the Sawchuk-Zaske method. (Sawchuk RJ, and Zaske DE. Pharmacokinetics of dosing regimens which utilize multiple intravenous infusion: Gentamicin in burn patients. *J Pharmacokin Biopharm* 1976; 4: 183-95)

The independent variables set forth in Table III were used in a stepwise multiple linear regression program to produce the models of best definition for K and V by entering each patients individual variables, V and K into the program. A linear least-squares regression model was then fitted to the entire set of independent variables to identify the best independent variables and their coefficients for the description of the two dependent variables, K and V. Insignificant variables were dropped from the model. Table III shows the model sequence used to solve for V and K as derived by the stepwise regression analysis. The equations generated are those set forth previously as Equation 1 and Equation 2.

TABLE III

| Sequence Number | Variable | Coefficient |
|---|---|---|
| A. Multiple Regression for Volume of Distribution | | |
| | intercept | 0.197 |
| 1 | age | 0.004 |
| 2 | reactance | −0.044 |
| 3 | phase angle | −9.935 |
| 4 | height/weight | 1.315 |
| 5 | height$^2$/weight × R | −1.678 |
| 6 | 1/weight | −121.730 |
| 7 | reactance/R | 587.580 |
| B. Multiple Regression for Elimination Rate Constant | | |

TABLE III-continued

| Sequence Number | Variable | Coefficient |
|---|---|---|
| | intercept | 0.802 |
| 1 | sex | −0.208 |
| 2 | age | −0.007 |
| 3 | reactance | 0.039 |
| 4 | phase angle | 7.285 |
| 5 | height$^2$/(weight × R) | 1.925 |
| 6 | 1/weight | 205.613 |
| 7 | height/weight | −1.858 |
| 8 | reactance/R | −434.405 |

Where R = resistance

Where phase angle = arc tan $\frac{\text{Reactance}}{R}$ in degrees

The linear least-squares regression program used for this data was SAS (SAS Users Guide: Statistics, Version 5 edition. Cary, N.C. 27611-8000. of SAS Institute Inc., 1985) Other internationally recognized programs could also be used and may include BMDP (Biomedical Data Processing) and SPSS (Statistical Programming for the Social Sciences).

In Table IV, elimination rate constants (K) and volumes of distribution (V) determined for gentamicin using a multiple regression analysis produced F variable sequence defined in Tables III and V are shown in columns B and D, respectively. Table V is the statistical analysis and resulting coefficients, standard errors and p-values (level of statistical significance) for determining (V) and (K) as derived by multiple regression analysis.

TABLE IV

Predicted and Measured Pharmacokinetic Parameters for Twelve Patients

| | Elimination Rate Constant | | Volume of Distribution | | Dose Calculated from Measured K,V | | Dose Calculated from Predicted K,V | |
|---|---|---|---|---|---|---|---|---|
| | Meas. | Pred. | Meas. | Pred. | Dose/T | mg/day | Dose/T | mg/day |
| | (hr −1) | | (1/kg) | | | | | |
| Pt. | A | B | C | D | E | F | G | H |
| 1 | .159 | .173 | .370 | .274 | 145 Q12 | 290 | 150 Q12 | 300 |
| 2 | .411 | .411 | .300 | .299 | 140 Q6 | 560 | 140 Q6 | 560 |
| 3 | .807 | .807 | .220 | .181 | 130 Q4 | 780 | 105 Q4 | 630 |
| 4 | .465 | .452 | .220 | .260 | 100 Q4 | 600 | 125 Q6 | 508 |
| 5 | .171 | .159 | .320 | .295 | 130 Q12 | 260 | 115 Q12 | 230 |
| 6 | .112 | .113 | .700 | .699 | 260 Q16 | 390 | 260 Q16 | 390 |
| 7 | .161 | .171 | .390 | .379 | 150 Q12 | 300 | 150 Q12 | 300 |
| 8 | .138 | .102 | .300 | .323 | 120 Q16 | 180 | 115 Q16 | 172.5 |
| 9 | .111 | .142 | .220 | .266 | 100 Q16 | 150 | 100 Q12 | 200 |
| 10 | .034 | .037 | .520 | .506 | 180 Q48 | 90 | 180 Q48 | 90 |
| 11 | .431 | .442 | .220 | .235 | 105 Q6 | 420 | 115 Q6 | 460 |
| 12 | .251 | .242 | .360 | .373 | 150 Q8 | 450 | 150 Q8 | 450 |
| mean | .270 | .270 | .345 | .349 | 142.5 | 372.5 | 142.1 | 357.5 |
| | .22 | .22 | .14 | .14 | 43.9 | 202.8 | 43.9 | 168.3 |
| | | NS | | NS | | | | NS |

TABLE V

Multiple Variable Regression Analysis Statistical Performance

| Volume Of Distribution - V | | |
|---|---|---|
| Sequence Number | Standard Error | P-Value |
| intercept | 0.320 | 0.572 |
| 1 | 0.001 | 0.023 |
| 2 | 0.010 | 0.014 |
| 3 | 2.152 | 0.010 |
| 4 | 0.376 | 0.025 |
| 5 | 0.479 | 0.025 |
| 6 | 38.665 | 0.035 |
| 7 | 122.961 | 0.009 |

For the model: R = 0.988 $R^2$ = 0.977 p-value < .005 C.V. = 10.09%

| Elimination Rate Constant - K | | |
|---|---|---|
| Sequence Number | Standard Error | P-Value |

TABLE V-continued

Multiple Variable Regression Analysis
Statistical Performance

| intercept | 0.291 | 0.070 |
|---|---|---|
| 1 | 0.045 | 0.019 |
| 2 | 0.001 | 0.009 |
| 3 | 0.010 | 0.028 |
| 4 | 1.962 | 0.034 |
| 5 | 0.442 | 0.022 |
| 6 | 35.651 | 0.010 |
| 7 | 0.347 | 0.013 |
| 8 | 112.242 | 0.031 |

For the model: R = 0.997 R² = 0.994 p-value < .003 C.V. = 11.80%

The values of (K) and (V) as determined through measured serum concentrations are recorded in columns A and C, respectively. The values of (K) and (V) determined using bioelectrical impedance in accordance with the present invention were then used to calculate a dosage regimen of gentamicin (an aminoglycoside) to produce a postdose serum concentration of 6.0 mcg/ml and a predose serum concentration of 1.0 mcg/ml as set forth in columns G and H. The (K) and (V) values determined through measured serum concentrations were also used to calculate a dosage regimen of gentamicin designed to produce a postdose concentration of 6.0 mcg/ml and predose concentration of 1.0 mcg/ml as set forth in columns E and F respectively. Calculation of (K) and (V) from the measured serum concentration data was performed as were the dosage regimens using the measured serum concentration data by the equations of Sawchuk and Zaske which will be known to those skilled in the art. Comparison of the pharmacokinetic parameters (K) and (V) and the dosage regimens with a two-sided T-test reveal no statistically significant differences between the determination of these values through the bioelectrical impedance method of the present invention and through actual measurement of serum concentration.

Serum concentrations were then simulated for an average 70 kg patient given a one-hour infusion of the dose to achieve a postdose serum concentration of 6.0 mcg/ml and a predose serum concentration of 1.0 mcg/ml. This simulation was performed with the values of (K) and (V) determined by measured serum concentrations and the calculated dosage regimen from these measured (K) and (V) values, is recorded, respectively, in columns A and B of Table VI. A simulation was also performed with the dosage regimen determined by the bioelectrical impedance analysis of the present invention, using the patient's actual measured (K) and (V), to test the prediction error of the method of dosing of the present invention. Equations A and B which were discussed earlier were used for calculating dosing interval and dose. The latter is recorded respectively in columns C and D of Table VI. There are no statistically significant differences between postdose or predose concentrations simulated from the measured (K) and (V) and those simulated from the values of (K) and (V) determined by the bioelectrical impedance analysis of the present invention.

TABLE VI

Comparison of Predicted Peak and
Trough Concentrations from
Measured vs. BIA Predicted Pharmacokinetic Parameters

| | Measured Parameters | | BIA Predicted Dose, Measured Parameters | |
|---|---|---|---|---|
| | Peak | Trough | Peak | Trough |
| | (mcg/ml) | | (mcg/ml) | |
| Pt. | A | B | C | D |
| 1 | 6.09 | .90 | 6.28 | .93 |
| 2 | 5.97 | .51 | 5.98 | .51 |
| 3 | 6.05 | .24 | 4.87 | .19 |
| 4 | 6.15 | .96 | 6.91 | .42 |
| 5 | 6.12 | .79 | 5.42 | .70 |
| 6 | 6.02 | 1.00 | 6.02 | 1.00 |
| 7 | 5.93 | .86 | 5.93 | .86 |
| 8 | 6.00 | .66 | 5.75 | .63 |
| 9 | 6.04 | 1.02 | 8.36 | 2.20 |
| 10 | 6.04 | 1.18 | 6.04 | 1.18 |
| 11 | 5.99 | .45 | 6.56 | .49 |
| 12 | 6.08 | .82 | 6.08 | .82 |
| mean | 6.04 | .78 | 6.18 | .82 |
| | .06 | .27 | .86 | .51 |
| | | NS | | |

EXAMPLE II

The following example again demonstrates, comparatively, pharmacokinetic parameters and calculated dosage regimens for prior art dosing methods against the bioelectrical impedance determined dosage regimens for the present invention. Fifteen normal adult males were used in the following study. Each subject was given a single intravenous dosage of theophylline.

Serial blood samples were obtained, for all fifteen patients, from an intravenous catheter placed in the arm. Samples were drawn immediately before and at 0.5, 1, 3, 5, 7 and 12 hours after a 30 minute infusion of theophylline (4 mg/kg of body weight). The blood was centrifuged and the serum separated and frozen at −20 degrees C. until the time of assay.

At the midpoint of the blood sampling period, the subjects were placed in the supine position on an insulative surface. The pre-gelled electrodes were attached to the patient such that one current electrode was attached to the dorsal surface of the patient's right hand at the distal metacarpals, one current electrode was attached to the patient's right foot at the location of the distal metatarsals, one detector electrode was connected to the patient's right wrist at the right pisiform prominence, and one detector electrode was placed on the patient's right ankle between the medial and lateral malleoli. An excitation current of 800 microamps and frequency of 50 kHz was then applied and (R) and (Xc) values obtained.

Both elimination rate constant and volume of distribution were determined by nonlinear regression analysis of the serum concentration data for each patient using Lagran (Rocci ML, and Jusko WJ: Lagran Program For Area and Moments In Pharmacokinetic Analysis, *Comput Programs Biomed* 1983; 16: 203–16).

The independent variables set forth in Table VII were used in a stepwise multiple linear regression program to produce the models of best definition for (Cl), (K) and (V) by entering each patients individual variables (Cl), (V) and (K) into the program. It then fits a linear least-squares regression model to the entire set of independent variables to identify the best independent variables and their coefficients for the description of the two dependent variables (Cl), (K) and (V). Insignificant variables were dropped from the model. The equations generated are those set forth previously as Equation 3, Equation 4 and Equation 5.

and p-values (level of statistical significance) for determining (Cl), (K), and (V) as derived by multiple regression analysis.

TABLE VIII

| Pt. | Clearance 1/hr | | Elimination Rate Constant, hr | | Volume of Distribution, 1. | | Dose Calculation from Measured Cl | Dose Calculated from Predicted |
|---|---|---|---|---|---|---|---|---|
| | Meas. A | Pred. B | Meas. C | Pred. D | Meas. E | Pred. F | Dose/T (mg/8 hour) G | Dose/T (mg/8 hour) H |
| 1 | 2.756 | 2.528 | .0885 | .0840 | 31.8 | 30.6 | 220 Q8 | 200 Q8 |
| 2 | 2.685 | 2.896 | .0631 | .0982 | 39.4 | 38.7 | 215 Q8 | 230 Q8 |
| 3 | 2.433 | 2.802 | .0591 | .0796 | 39.8 | 38.1 | 195 Q8 | 225 Q8 |
| 4 | 3.048 | 2.918 | .0521 | .0549 | 55.4 | 57.0 | 245 Q8 | 235 Q8 |
| 5 | 4.267 | 4.129 | .0813 | .0549 | 51.0 | 52.5 | 340 Q8 | 330 Q8 |
| 6 | 3.478 | 3.453 | .0895 | .0879 | 37.7 | 37.8 | 280 Q8 | 275 Q8 |
| 7 | 4.219 | 4.365 | .1241 | .1141 | 33.0 | 30.9 | 340 Q8 | 350 Q8 |
| 8 | 2.091 | 2.156 | .0305 | .0405 | 65.6 | 65.1 | 165 Q8 | 175 Q8 |
| 9 | 3.048 | 2.925 | .0813 | .0942 | 37.2 | 36.4 | 245 Q8 | 235 Q8 |
| 10 | 3.600 | 3.241 | .1895 | .1052 | 21.8 | 28.8 | 290 Q8 | 260 Q8 |
| 11 | 2.819 | 2.719 | .0815 | .1092 | 34.6 | 33.5 | 225 Q8 | 220 Q8 |
| 12 | 4.114 | 4.265 | .0938 | .0746 | 42.0 | 40.9 | 330 Q8 | 340 Q8 |
| 13 | 3.009 | 2.876 | .0921 | .0945 | 30.9 | 31.9 | 240 Q8 | 230 Q8 |
| 14 | 3.661 | 3.732 | .0713 | .0726 | 50.9 | 49.7 | 295 Q8 | 300 Q8 |
| 15 | 1.836 | 2.061 | .0774 | .1063 | 20.4 | 19.3 | 145 Q8 | 165 Q8 |
| MEAN | 3.137 | 3.137 | .0850 | .0850 | 39.4 | 39.4 | 251 Q8 | 251 Q8 |
| + SD | .745 | .718 | .035 | .021 | 12.2 | 12.0 | 60.5 | 57.2 |
| | | NS | | NS | | NS | | NS |

TABLE VII

A. Multiple Regression for Volume of Distribution

| Sequence Number | Variable | Coefficient |
|---|---|---|
| 1 | intercept | −65.64 |
| 2 | age | −1.03 |
| 3 | height | −1.05 |
| 4 | lean body weight | 2.54 |
| 5 | 1000 (1/weight) | −5.53 |
| 6 | 100 (reactance/weight) | 1.29 |
| 7 | 100 (reactance/resistance) | 18.63 |
| 8 | 10,000 (reactance/resistance)$^3$ | −5.43 |

B. Multiple Regression for Clearance

| Sequence Number | Variable | Coefficient |
|---|---|---|
| 1 | intercept | −65.17 |
| 2 | height | 0.98 |
| 3 | lean body weight | −1.95 |
| 4 | reactance | 3.15 |
| 5 | resistance | −0.38 |
| 6 | weight | 1.08 |
| 7 | 1000 (1/weight) | 8.28 |
| 8 | 100 (reactance/weight) | −0.95 |
| 9 | 100 (reactance/resistance) | −7.54 |
| 10 | 10,000 (reactance/resistance)$^3$ | −0.62 |

C. Multiple Regression for Elimination Rate constant

| Sequence Number | Variable | Coefficient |
|---|---|---|
| 1 | intercept | 0.03 |
| 2 | 1/weight | −9.78 |

[Note that the variables (1/weight), (reactance/weight), (reactance/resistance), and (reactance/resistance)$^3$ were multiplied by a factor of 100 or 1000 after regression analysis to simplify their respective coefficients without the need to place the coefficients in semi-exponential notation i.e. to convert .00828 to 8.28 etc.]

The linear least-squares regression program used for this data was SAS (SAS Users Guide: Statistics, Version 5 edition. Cary, N.C. 27611-8000. of SAS Institute Inc., 1985). Other internationally recognized programs could also be used and may include BMDP (Biomedical Data Processing) and SPSS (Statistical Programming for the Social Sciences).

In Table VIII, clearance (Cl), elimination rate constant (K), and volume of distribution (V), determined for theophylline using a multiple regression analysis produced F variable sequence defined in Tables VII and IX are shown in columns B, D, and F, respectively. Table VII is the model sequence used to solve for (Cl), (K) and (V) as derived by stepwise regression analysis. Table IX is the statistical analysis, standard deviations

TABLE IX

Multiple Variable Regression Analysis
Statistical Performance

Volume of Distribution - V

| Sequence Number | Standard Deviation | P-Value |
|---|---|---|
| 1 | 88.47 | 0.482 |
| 2 | 0.26 | 0.006 |
| 3 | 0.24 | 0.004 |
| 4 | 0.57 | 0.003 |
| 5 | 1.67 | 0.013 |
| 6 | 0.30 | 0.004 |
| 7 | 5.46 | 0.011 |
| 8 | 1.55 | 0.010 |

For the model: R = 0.983 R$^2$ = 0.966 p-value greater than 0.001 C.V. = 8.06%

Clearance - Cl

| Sequence Number | Standard Deviation | P-Value |
|---|---|---|
| 1 | 26.14 | 0.054 |
| 2 | 0.14 | 0.001 |
| 3 | 0.34 | 0.002 |
| 4 | 0.77 | 0.010 |
| 5 | 0.06 | 0.002 |
| 6 | 0.16 | 0.000 |
| 7 | 2.38 | 0.018 |
| 8 | 0.29 | 0.022 |
| 9 | 1.92 | 0.011 |
| 10 | 0.18 | 0.020 |

For the model: R = 0.964 R$^2$ = 0.930 p-value greater than 0.020 C.V. = 10.52%

Elimination Rate Constant

| Sequence Number | Standard Deviation | P-Value |
|---|---|---|
| 1 | 0.04 | 0.503 |
| 2 | 3.63 | 0.018 |

For the model: R = 0.599 R$^2$ = 0.358 p-value greater than 0.018 C.V. = 35.16%

The values (K), (V), and (Cl) as determined through measured serum concentrations are recorded in columns A, C, and E, respectively. The value of (Cl) determined using bioelectrical impedance in accordance with the present invention was then used to calculate a dosage regimen of theophylline (a bronchodilator) to produce an average steady state serum concentration of 10 mcg/ml set forth in column H. The (Cl) value determined through measured serum concentrations was also used to calculate a dosage regimen of theophylline designed to produce an average steady state serum concentration of 10 mcg/ml as set forth in column G. Calculation of (Cl) from the measured serum concentration data was performed as were the dosage regimens using the measured serum concentration data by the standard pharmacokinetic equation:

$$Css = \frac{F \, dose}{Cl \, T}$$

where Css=average steady state serum concentration mcg/ml.

F=1.0, assuming 100% oral absorption
Cl=clearance, 1/hr,
T=dosing interval, hours.

Comparison of the pharmacokinetic parameters (K), (V), and (Cl) and the dosage regimens with a two-sided t-test reveal no statistically significant differences between determination of these values through the bioelectrical impedance method of the present invention and through actual measurement of serum concentrations.

What is claimed is:

1. A method for determining a therapeutic drug dosage regimen for a biological subject which comprises the steps of:

providing a first equation which relates at least one of the following personal characteristics, resistance, reactance, age, height, weight and sex of the subject, to a predictive value for volume of distribution (V) for a preselected drug in said subject;

providing a second equation which relates at least one of the following personal characteristics, resistance, reactance, age, height, weight and sex of said subject, to a predictive value for elimination rate constant (K) for said preselected drug in said subject;

determining the value of said personal characteristics of said subject which are related to said first equation for the predictive value for V;

determining the value of said personal characteristics of said subject which are related to said second equation for the predictive value for K;

calculating said predictive value of V using said first equation and said value of said measured personal characteristics related to said first equation;

calculating said predictive value of K using said second equation and said value of said measured personal characteristics related to said second equation;

determining a desired therapeutic concentration of said preselected drug for said subject; and calculating a dose and dosing interval to obtain said therapeutic concentrations of said drug using said calculated predictive values of V and K.

2. The method for determining a therapeutic drug dosage regimen for a biological subject recited in claim 1, further including the steps of:

providing a third equation which relates at least one of the following personal characteristics, resistance, reactance, age, height, weight and sex of said subject, to a predictive value for clearance (CL) for said drug in said subject;

determining the value of said personal characteristics of said subject which are related to said third equation for the predictive value for CL;

calculating said predictive value of CL using said third equation and said value of said measured personal characteristics related to said third equation; and using said calculated predictive value of CL in said dose and dosing interval calculating step in addition to said calculated predictive values of V and K.

3. The method for determining a therapeutic drug dosage regimen recited in claim 1, wherein said steps of determining the value of said personal characteristics related to said first equation and determining the value of said personal characteristics related to said second equation include the steps of attaching at least one current electrode and at least one detector electrode to said subject, said current electrode and said detector electrode being in electrical communication with an impedance plethysmograph;

flowing an excitation current through a portion of said subject's body with said impedance plethysmograph and said current electrode;

detecting the voltage drop of said current with said detector electrode and said impedance plethysmograph; and determining said resistance and said reactance from said voltage drop with said impedance plethysmograph.

4. A method for determining a therapeutic drug dosage regiment for a biological subject comprising the steps of:

generating equations which relate resistance (R) and reactance (Xc) to volume of distribution (V) and elimination rate constant (K) for a preselected drug measuring the resistance (R) and reactance (Xc) of a subject by bioelectric impedance analysis;

solving said equations for V and K by utilizing said measured values of R and Xc;

determining a dosage regiment for said subject for said preselected drug by utilizing the values of V and K determined in said equation solving step.

5. The method for determining a therapeutic drug dosage regiment for a biological subject recited in claim 4, wherein said generating step includes analyzing preselected independent variables, including said resistance (R) and reactance (Xc) by a linear regression method.

6. The method for determining a therapeutic drug dosage regiment for a biological subject recited in claim 4, further including the steps of generating an equation which relates said resistance (R) and reactance (Xc) to clearance (CL), solving said equation for CL and utilizing said value of CL obtained in said CL equation solving step in said dosage determining step.

7. The method for determining a therapeutic drug dosage regimen for a biological subject recited in claim 6, wherein said step of attaching said current electrode and said detector includes attaching said current electrode and said detector electrode ipsilaterally on said subject.

8. The method for determining a therapeutic drug dosage regimen for a biological subject recited in claim 6, wherein said flowing step includes flowing a current of about 800 microamps and from about 100 Hz to 1 MHz through said subject's body.

9. The method for determining a therapeutic drug dosage regimen for a biological subjected recited in claim 6, wherein said generating steps include analyzing preselected independent variables, including said resistance (R) and reactance (Xc) by a linear regression method.

10. A method for calculating a drug dosage regimen for a human subject comprising the steps of measuring the values of resistance (R) and reactance (Xc) for a human subject and determining a drug dosage regimen for a preselected drug for said human subject by utilizing said measured values of said resistance (R) and reactance (Xc).

11. A non-invasive method for determining the drug dose and dosing interval for a given drug to produce a preselected therapeutic concentration profile of a drug in a subject comprising the steps of determining the age, sex, weight, and height of the subject;
measuring the bioelectrical impedance of the subject using a bioelectrical impedance plethysmograph;
determining the resistance and reactance components of said measured bioelectrical impedance;
determining the volume of distribution and elimination rate constant characteristics of said drug;
selecting said therapeutic concentration profile to be produced in the subject;
determining said volume of distribution value and said elimination rate constant value for the subject patient using said measured values of resistance and reactance and said values for said subject's age, sex, height, and weight for said drug; and
calculating said dose and said dosing interval for said drug for the subject to produce said preselected therapeutic drug concentration profile based on said determined values of said volume of distribution and said elimination rate constant.

* * * * *